US006461808B1

United States Patent
Bodner et al.

(10) Patent No.: US 6,461,808 B1
(45) Date of Patent: Oct. 8, 2002

(54) PIPETTE-LOADED BIOASSAY ASSEMBLY FOR DETECTING MOLECULAR OR CELLULAR EVENTS

(75) Inventors: Kevin S. Bodner, Belmont, CA (US); Andrew P. Sandham, Woodside, CA (US)

(73) Assignee: Signature BioScience, Inc., San Francisco, CA (US)

( * ) Notice: Subject to any disclaimer, the term of this patent is extended or adjusted under 35 U.S.C. 154(b) by 0 days.

(21) Appl. No.: 09/880,746

(22) Filed: Jun. 12, 2001

(51) Int. Cl.$^7$ ................................................. C12Q 1/00

(52) U.S. Cl. ................................ 435/4; 435/6; 435/7.1; 435/287.1; 435/287.2; 436/43; 436/54; 422/68.1; 422/100; 422/102; 422/104

(58) Field of Search .......................... 422/58, 63, 68.1, 422/82.11, 100, 119, 186.3, 102, 104; 435/287.1, 287.2, 280.7, 287.3, 288.5, 272.1, 6, 7.1; 436/43, 54, 52, 517

(56) References Cited

U.S. PATENT DOCUMENTS

| | | | |
|---|---|---|---|
| 5,025,222 A | 6/1991 | Scott et al. ................. 324/639 |
| 5,156,810 A | 10/1992 | Ribi ......................... 422/82.01 |
| 5,363,052 A | 11/1994 | McKee ....................... 324/663 |
| 5,653,939 A | 8/1997 | Hollis et al. .................... 422/50 |
| 5,858,666 A | 1/1999 | Weiss ............................ 435/6 |
| 5,900,618 A | 5/1999 | Anlage et al. ............. 250/201.3 |
| 5,966,017 A | 10/1999 | Scott et al. ................. 324/639 |
| 6,013,528 A | * | 1/2000 | Jacobs et al. .................. 436/54 |
| 6,048,692 A | 4/2000 | Maracas et al. ................. 435/6 |
| 6,287,874 B1 | * | 9/2001 | Hefti et al. ................... 436/501 |

FOREIGN PATENT DOCUMENTS

| | | | |
|---|---|---|---|
| DE | WO 01/27610 | * | 4/2001 |
| EP | 0 519 250 A2 | | 12/1992 |

OTHER PUBLICATIONS

Ajmera et al., "Microwave measurements with active systems", Proceeding of the IEEE, 62(1): 118–127.
Altschuler, H.M. 1963. Dielectric Constant. Handbook of Microwave Measurements (M. Sucher & J. Fox, eds.). Brooklyn, Polytechnic Press, New York, NY. Vo. 2:530–536.
Amo et al., "Dielectric measurements of lysozyme and tri–N–acetyl–D–glucosamine association at radio and microwave frequencies", Biosensors & Bioelectronics, 12(9–10):953–958 (1997).
Esselle et al., "Capacitive sensors for in–vivo measurements of the dielectric properties of biological materials", IEEE Transactions on Instrumentation and Measurement, 37(1):101–105 (1988).
Facer et al., "Dielectric spectroscopy for bioanalysis: From 40 Hz to 26.5 GHz in a microfabricated wave guide", Appl. Phys. Lett., 78(7)996–998.

(List continued on next page.)

Primary Examiner—Long V. Le
Assistant Examiner—Gary W. Counts
(74) Attorney, Agent, or Firm—Clifford Perry; Richard Neeley

(57) ABSTRACT

A pipette-loaded bioassay includes a measurement probe and a pipette tip. The measurement probe includes a probe head configured to launch an incident test signal and a connecting end configured to receive the incident test signal from a signal source. The pipette tip includes a sample interrogation region which is electromagnetically coupled to the probe head, the sample interrogation region configured to retain a plug of sample solution and constructed from a material which is substantially transparent to the incident test signal. The incident test signal electromagnetically couples through the sample interrogation region and to the molecular or cellular events occurring within the sample solution. The interaction of the incident test signal with the molecular or cellular events produces a modulated test signal which can be recovered and used to identify the molecular or cellular events occurring in a subsequently tested sample.

12 Claims, 6 Drawing Sheets

OTHER PUBLICATIONS

Gallone, "A fast and precise method for the measurement of dielectric permittivity at microwave frequencies", Journal of Microwave Power and Electromagnetic Energy, 3(3):158–164 (1996).

Goodwin et al., "Reentrant Radio–Frequency Resonator for Automated Phase–Equilibria and Dielectric Measurements in Fluids", Rev. Sci. Instrum. 67(12):4294–4303 (1996).

Hefti et al., "Sensitive detection method of dielectric dispersions in aqueous–based, surface–bound macromolecular structures using microwave spectroscopy", Appl. Phys. Lett., 75(12) 1802–1804 (1999).

Hollis et al., "A swept–frequency magnitude method for the dielectric characterization of chemical and biological systems", IEEE, vol. MTT–28, No. 7, Jul. 1980, pp. 791–801.

McKee et al., "Real–time chemical sensing of aqueous ethanol glucose mixtures", IEEE Transactions on Instrumentation and Measurement, vol. 49, No. 1, Feb. 2000, pp. 114–119.

Stuchly et al., "Coaxial line reflection methods for measuring dielectric properties of biological substances at radio and microwave frequencies—A review", IEEE Transactions on Instrumentation and Measurement, vol. IM–29, No. 3, Sep. 1980, pp. 176–183.

Wichaidit et al., "Resonant slot antennas as transducers of DNA hybridization: A computational feasibility study", IEEE–MTT, May 2001, MTT Conference in Phoenix, AZ.

\* cited by examiner

PIPETTE-LOADED BIOASSAY ASSEMBLY FOR DETECTING MOLECULAR OR CELLULAR EVENTS

BACKGROUND OF THE INVENTION

The present invention relates to bioassay devices, and more particularly to a pipette-loaded bioassay assembly operable to detect and identify molecular and cellular activity in a sample solution.

The applicant, in PCT publication number WO 99/39190, has previously discussed the need of a system to determine the ability of molecules of interest to interact with other molecules. Likewise, the ability to detect the physical and functional properties of biological molecules and cells on a small scale is highly desirable. Such molecular interactions, as well as the detection of functional and physical properties of these biological molecules and cells in an aqueous environment are referred to here as "molecular events" and "cellular events," respectively.

The occurrence of molecular or cellular events in a test sample can be detected by illuminating the test sample with an electromagnetic test signal and recovering the resulting modulated signal, the modulation being indicative of the molecular or cellular event occurring within the sample. The applicant has presented several bioassay structures capable of this process in PCT publication nos. WO 01/20239 and WO 01/27610 in addition to the aforementioned publication.

The applicant has additionally described various sample handling structures used to supply sample to the bioassay structure. Exemplary structures include microfluidic devices, flow tubes, flow cells, and sample cavities.

In addition to these sample handling structures, pipette tips are commonly used to transport sample. For example, automated sample processors are often equipped with pipette tips for transporting sample to/from bioassay structures. These systems are advantageous in that they can aspirate, transport, and dispense small, precise amounts of sample to one or more bioassay devices at high speeds for extended periods of time without human intervention.

What is therefore needed is a pipette-compatible bioassay assembly that is operable to detect molecular and cellular events using applicant's technique of illuminating the supplied sample with an electromagnetic signal.

SUMMARY OF THE INVENTION

The present invention provides a pipette-loaded bioassay assembly operable to identify molecular or cellular events in a test sample. In one embodiment, the pipette-loaded bioassay assembly includes a measurement probe and a pipette tip. The measurement probe includes a probe head configured to launch an incident test signal and a connecting end configured to receive the incident test signal from a signal source. The pipette tip includes a sample interrogation region which is electromagnetically coupled to the probe head, the sample interrogation region configured to retain a plug of sample solution and constructed from a material which is substantially transparent to the incident test signal. The incident test signal electromagnetically couples through the sample interrogation region and to the molecular or cellular events occurring within the sample solution. The interaction of the incident test signal with the molecular or cellular events produces a modulated test signal which can be recovered and used to identify the molecular or cellular events occurring in a subsequently tested sample.

Other advantages and aspects of the invention will be apparent when considered in view of the following drawings and description.

BRIEF DESCRIPTION OF THE DRAWINGS

For simplicity, components used in previous drawings are labeled with their corresponding numerals.

DESCRIPTION OF THE SPECIFIC EMBODIMENTS

Definitions

Figure 1:
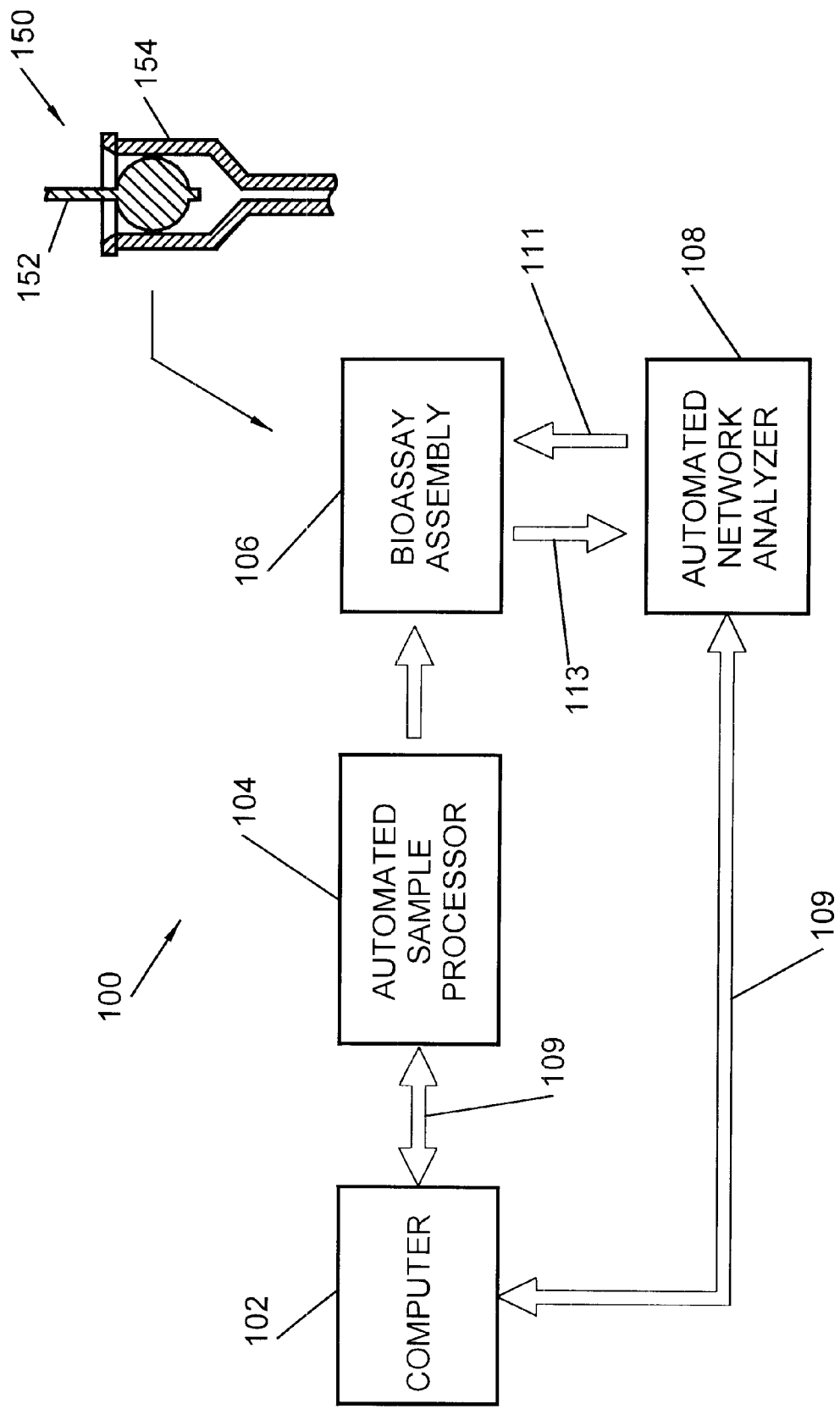
FIG. 1 illustrates a simplified block diagram of a pipette-loaded bioassay test system in accordance with the present invention.

As used herein, the term "molecular binding event" (sometimes shortened to "binding event" or "binding") refers to the interaction of a molecule of interest with another molecule. The term "molecular structure" refers to all structural properties of molecules of interest, including the presence of specific molecular substructures (such as alpha helix regions, beta sheets, immunoglobulin domains, and other types of molecular substructures), as well as how the molecule changes its overall physical structure via interaction with other molecules (such as by bending or folding motions), including the molecule's interaction with its own solvation shell while in solution. Together, "molecular structures" and "molecular binding events" are referred to as "molecular events." The simple presence of a molecule of interest in the region where detection/analysis is taking place is not considered to be a "molecular event," but is referred to as a "presence."

Examples of molecular binding events are (1) simple, non-covalent binding, such as occurs between a ligand and its antiligand, and (2) temporary covalent bond formation, such as often occurs when an enzyme is reacting with its substrate. More specific examples of binding events of interest include, but are not limited to, ligand/receptor, antigen/antibody, enzyme/substrate, DNA/DNA, DNA/RNA, RNA/RNA, nucleic acid mismatches, complementary nucleic acids and nucleic acid/proteins. Binding events can occur as primary, secondary, or higher order binding events. A primary binding event is defined as a first molecule binding (specifically or non-specifically) to an entity of any type, whether an independent molecule or a material that is part of a first surface, typically a surface within the detection region, to form a first molecular interaction complex. A secondary binding event is defined as a second molecule binding (specifically or non-specifically) to the first molecular interaction complex. A tertiary binding event is defined as a third molecule binding (specifically or non-specifically) to the second molecular interaction complex, and so on for higher order binding events.

Examples of relevant molecular structures are the presence of a physical substructure (e.g., presence of an alpha helix, a beta sheet, a catalytic active site, a binding region, or a seven-trans-membrane protein structure in a molecule) or a structure relating to some functional capability (e.g., ability to function as an antibody, to transport a particular ligand, to function as an ion channel (or component thereof), or to function as a signal transducer).

Molecular structure is typically detected by comparing the signal obtained from a molecule of unknown structure and/or function to the signal obtained from a molecule of known structure and/or function. Molecular binding events are typically detected by comparing the signal obtained from a sample containing one of the potential binding partners (or the signals from two individual samples, each containing one of the potential binding partners) to the signal. obtained from a sample containing both potential binding partners. Together, the detection of a "molecular binding event" or "molecular structure" is often referred to as "molecular detection."

The term "cellular event" refers in a similar manner to reactions and structural rearrangements occurring as a result of the activity of a living cell (which includes cell death). Examples of cellular events include opening and closing of ion channels, leakage of cell contents, passage of material across a membrane (whether by passive or active transport), activation and inactivation of cellular processes, as well as all other functions of living cells. Cellular events are commonly detected by comparing modulated signals obtained from two cells (or collection of cells) that differ in some fashion, for example by being in different environments (e.g., the effect of heat or an added cell stimulant) or that have different genetic structures (e.g., a normal versus a mutated or genetically modified cell). Morpholic changes are also cellular events. The same bioassay systems can be used for molecular and cellular events, differing only in the biological needs of the cells versus the molecules being tested. Accordingly, this specification often refers simply to molecular events (the more difficult of the two measurements under most circumstances) for simplicity, in order to avoid the awkwardness of continually referring to "molecular and/or cellular" events, detection, sample handling, etc., when referring to an apparatus that can be used to detect either molecular events or cellular events. When appropriate for discussion of a particular event, the event will be described as, for example, a cellular event, a molecular binding event, or a molecular structure determination. When used in a claim, "molecular event" does not include "cellular event" and both are specified if appropriate.

The methodology and apparatuses described herein are primarily of interest to detect and predict molecular and cellular events of biological and pharmaceutical importance that occur in physiological situations (such as in a cellular or subcellular membrane or in the cytosol of a cell). Accordingly, structural properties of molecules or interactions of molecules with each other under conditions that are not identical or similar to physiological conditions are of less interest. For example, formation of a complex of individual molecules under non-physiological conditions, such as would be present in the vacuum field of an electron microscope or in gaseous phase mixtures, would not be considered to be a preferred "molecular binding event," as this term is used herein. Here preferred molecular events and properties are those that exist under "physiological conditions," such as would be present in a natural cellular or intercellular environment, or in an artificial environment, such as in an aqueous buffer, designed to mimic a physiological condition. It will be recognized that local physiological conditions vary from place to place within cells and organisms and that artificial conditions designed to mimic such conditions can also vary considerably. For example, a binding event may occur between a protein and a ligand in a subcellular compartment in the presence of helper proteins and small molecules that affect binding. Such conditions may differ greatly from the physiological conditions in serum, exemplified by the artificial medium referred to as "normal phosphate buffered saline" or PBS. Preferred conditions of the invention will typically be aqueous solutions at a minimum, although some amounts of organic solvents, such as DMSO, may be present to assist solubility of some components being tested. An "aqueous solution" contains at least 50 wt. % water, preferably at least 80 wt. % water, more preferably at least 90 wt. % water, even more preferably at least 95 wt. % water. Other conditions, such as osmolarity, pH, temperature, and pressure, can and will vary considerably in order to mimic local conditions of the intracellular environment in which, for example, a binding event is taking place. The natural conditions in, for example, the cytosol of a cell and a lysosome of that cell, are quite different, and different artificial media would be used to mimic those conditions. Examples of artificial conditions designed to mimic natural ones for the study of various biological events and structures are replete in the literature. Many such artificial media are sold commercially, as exemplified by various scientific supply catalogues, such as the 2000/2001 issue of the Calbiochem General Catalogue, pages 81–82, which lists 60 commercially available buffers with pH values ranging from 3.73 to 9.24 typically used in biological investigations. Also see general references on the preparation of typical media, such as chapter 7 ("The Culture Environment") of *Culture of Animal Cells: A Manual of Basic Techniques,* Third Edition, R. Ian Freshney, Wiley-Liss, New York (1994).

As used herein, the term "test sample" refers to the material being investigated (the analyte) and the medium/buffer in which the analyte is found. The medium or buffer can included solid, liquid or gaseous phase materials; the principal component of most physiological media/buffers is water. Solid phase media can be comprised of naturally occurring or synthetic molecules including carbohydrates, proteins, oligonucleotides, $SiO_2$, GaAs, Au, or alternatively, any organic polymeric material, such as Nylon®, Rayon®, Dacryon®, polypropylene, Teflon®, neoprene, delrin or the like. Liquid phase media include those containing an aqueous, organic or other primary components, gels, gases, and emulsions. Exemplary media include celluloses, dextran derivatives, aqueous solution of d-PBS, Tris, deionized water, blood, cerebrospinal fluid, urine, saliva, water, and organic solvents.

As used herein, the term "electromagnetically coupled" refers to the transfer of electromagnetic energy between two objects, e.g., the reentrant post and molecular events occurring within the test sample. The two objects can be electromagnetically coupled when the objects are in direct contact, (e.g., molecular events occurring along the surface of a reentrant post), or when the objects are physically separated from each other (e.g., molecular events occurring within a sample flowing through a flow tube, the flow tube positioned within the detection region). As a modification, the term "electromagnetically couples" will indicate the interaction of an electromagnetic signal (e.g., the incident test signal) with an object (e.g., molecular events occurring within the test sample).

As used herein, the term "test signal" refers to a sub-optical, time-varying electromagnetic signal. In specific embodiments, the test signal is preferably at or above 1 MHz ($1 \times 10^6$ Hz) and at or below 1000 GHz ($1 \times 10^{12}$ Hz), such as 10 MHz, 20 MHz, 45 MHz, 100 MHz, 500 MHz, 1 GHz ($1 \times 10^9$ Hz), 2 GHz, 5 GHz, 7.5 GHz, 10 GHz, 12 GHz, 15 GHz, 18 GHz, 20 GHz, 25 GHz, 30 GHz, 44 GHz, 60 GHz, 110 GHz, 200 GHz, 500 GHz, or 1000 GHz and range anywhere therebetween. A preferred region is from 10 MHz to 110 GHz, a more particularly from 45 MHz to 20 GHz. "Test signal" can refer to a range of frequencies rather than a single frequency, and such a range can be selected over any terminal frequencies, including frequency ranges bounded by the specific frequencies named in this paragraph. When referring to the detected range (or multiple) of modulated signals obtained after a range of frequencies has been coupled to a test sample, the term "spectrum" is sometimes used. An "incident test signal" is a test signal that originates from the signal source and is destined for the detection region for interaction with the sample. A "modulated test signal" is a test signal that has previously interacted with the test sample and is destined for a signal detector that can recover the modulation imparted by the signal interaction with the sample.

As used herein, the term "waveguide transmission structure" refers to a structure which supports the propagation of a waveguide mode signal, for instance, a transverse electric (TE) or transverse magnetic (TM) signal as known to those of skill in the area of microwave engineering. The waveguide transmission structure may consist of any conventional waveguide, for example, enclosed rectangular or circular waveguides or an unenclosed surface waveguide.

As used herein, the terms "transverse electromagnetic transmission structure" or "TEM structure" refer to a structure which supports the propagation of a transverse electromagnetic (TEM) signal as known in the art of microwave engineering. Such structures include a signal plane, a ground plane, and a dielectric layer interposed between the signal and ground planes. Exemplary structures include microstrip, stripline, coplanar waveguide, coaxial cable, and slot line structures.

System Overview

FIG. 1 illustrates a simplified block diagram of a pipette-loaded bioassay test system 100 in accordance with the present invention. The system 100 includes a computer 102, an automated sample processor 104, a bioassay assembly 106, and an automated network analyzer 108. Control and data bus lines 109 are connected between the computer 102, the sample processor 104, and network analyzer 108 as shown. A pipette assembly 150 extends from the automated sample processor 104 and includes a pipette tip 154 releasably attached to a pipette stem 152.

The automated sample processor 104 is operable to supply sample to, and position the pipette assembly 150 such that the pipette tip 154 is electromagnetically coupled to a bioassay device (shown and described below). The bioassay device/pipette tip arrangement is referred to herein as a bioassay assembly 106 and several embodiments are illustrated and described below. The automated sample processor 104 may be any of a variety of commercially available sample processor machines including model no. Biomek 2000 Laboratory Automation Workstation manufactured by Beckman Coulter, Inc. (Fullerton, Calif.), model no. Multiprobe II manufactured by the Packard Instrument Company (Downer's Grove, Ill.), and model Genesis RSP 150 manufactured by Tecar AG. (Hombrechtikon, Switzerland).

Once the pipette tip 154 is filled and positioned, the computer 102 controls the automated network analyzer 108 to generate and launch an incident test signal 111 at one or more test frequencies. The incident test signal 111 is guided to the sample solution where the incident test signal 111 illuminates the sample solution. Molecular or cellular events occurring within the sample solution operate to modulate the incident test signal 111, the modulation (typically changes in the signal's amplitude and/or phase) being indicative of the particular molecular or cellular events occurring within the sample solution. The modulated test signal 113 is recovered by the network analyzer 108 and the signal response of the bioassay assembly 106 is ascertained (typically by taking the ratio of the modulated signal to the incident signal). This signal response is then compared with one or more previously obtained signal responses in which the sample's molecular or cellular event composition is known. A high degree of correlation between the measured and one of the stored signal responses serves to positively identify the molecular or cellular events occurring with the sample solution. The aforementioned signal response may be represented in a variety of forms, for instance as scattering ("s") parameters or impedance ("z") parameters of the bioassay assembly. Additionally, the signal response may be converted into quantities, such as permittivity, that describe the material properties of the measured sample itself. In a specific embodiment, the signal response is converted into a "delta permittivity" value defined as the change in permittivity (real and/or imaginary components) of the measured sample relative to a reference sample. Other measurement formats may be used, and accordingly, the apparatus of the present invention is not limited to any specific measurement format or methodology described herein.

Pipette Tip Embodiments

Figure 2A:
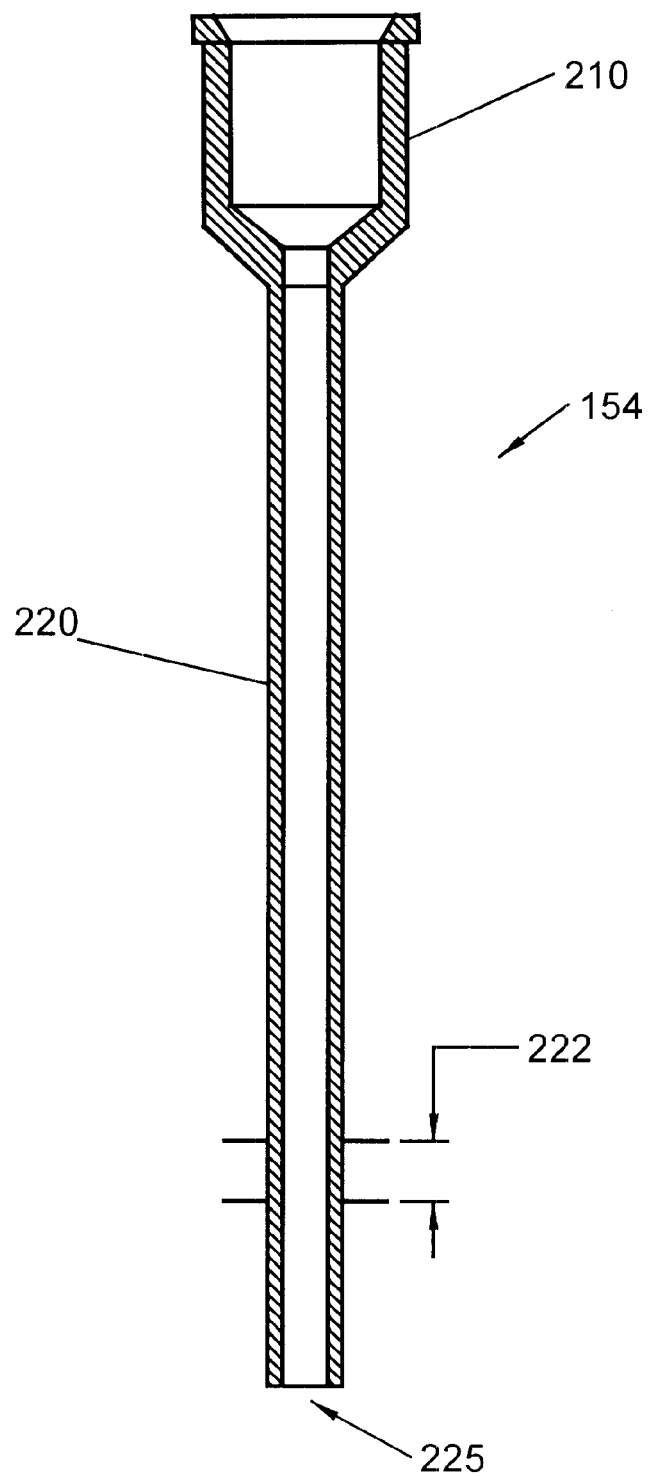
FIG. 2A illustrates a needle pipette tip in accordance with one embodiment of the pipette tip shown in FIG. 1.

FIG. 2A illustrates a needle pipette tip in accordance with one embodiment of the pipette tip 154 shown in FIG. 1. The needle pipette tip 154 includes an annular attachment flange 210 designed to be releasably engaged to the pipette stem (not shown) and a tubular section 220. The tubular section 220 includes a sample interrogation region 222 in which one or more plugs of the sample solution are retained when the pipette tip is illuminated by the incident test signal. The tubular section 220 includes a bottom opening 225 operable for aspirating sample solution into (or dispensing the sample solution from) the pipette tip, the process of which is further described below. Preferably, the tubular section 220 is constructed from a material that is substantially transparent to the incident and modulated test signals, i.e., has a low dielectric loss factor over the desired frequency of operation. Further preferably, the tubular section 220 is sized to retain one or more sample plugs, each having a volume of less than 100 $\mu$l, and more preferably 1–10 $\mu$l. In one embodiment, the needle pipette tip 154 is fabricated from tetrafluoroethylene (Teflon®) having a maximum dielectric loss factor of $1\times10^{-3}$ at 10 MHz, and the tubular section 220 measures 1.27 mm outer diameter, 0.80 mm inner diameter, and 75 mm in length. Similar materials such as polypropylene, polymers, hard plastics, glass, etc. can be used in alternative embodiments.

Figure 2B:
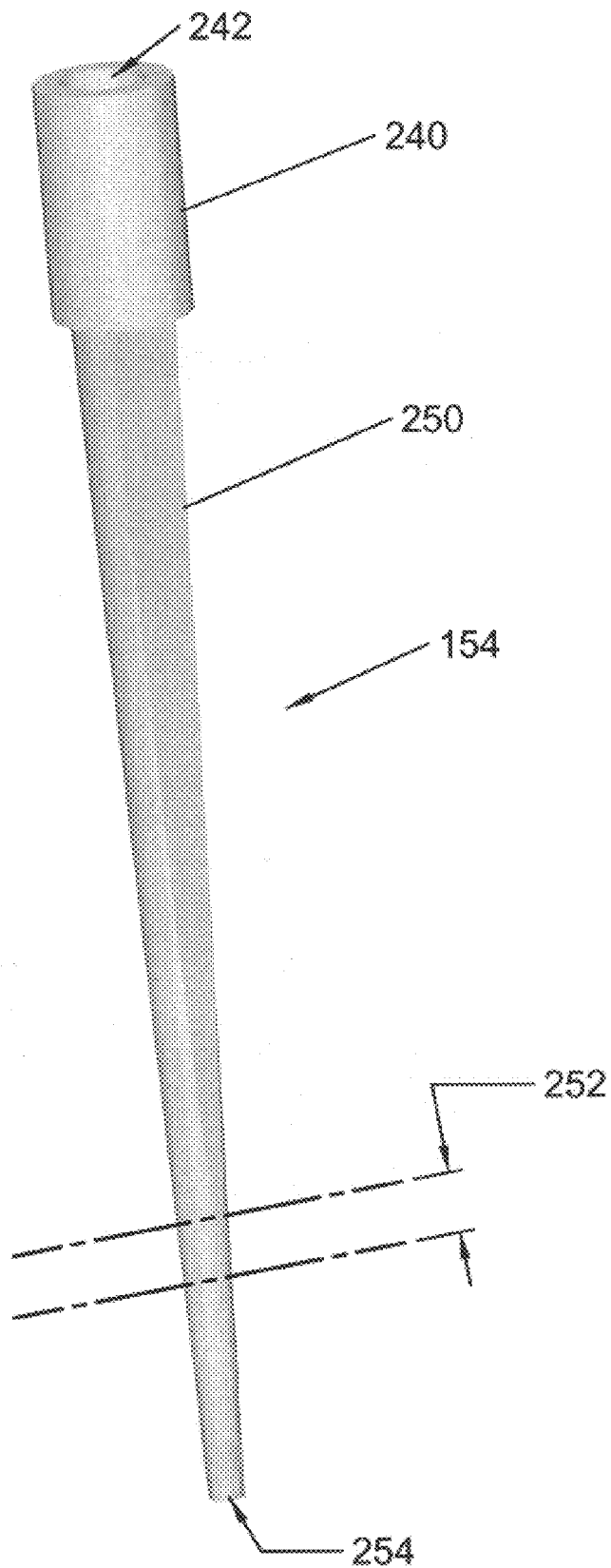
FIG. 2B illustrates a tapered pipette tip in accordance with one embodiment of the pipette tip shown in FIG. 1.

FIG. 2B illustrates a tapered pipette tip in accordance with one embodiment of the pipette tip 154 shown in FIG. 1. Similar in construction to the needle pipette tip, the tapered pipette tip includes an annular attachment flange 240 and a tapered section 250. The tapered section 250 includes a sample interrogation region 252 which retains the sample solution during incident test signal illumination of the pipette tip 154. The tapered section 250 includes a bottom opening 254 for aspirating sample solution into (or dispensing the sample solution from) the pipette tip, the process of which is further described below. One or more surfaces of the tapered section 250 may be made substantially flat to mate securely with a bioassay device, as further illustrated in FIG. 4 below. Preferably, the tapered section 250 is constructed from a material that is substantially transparent to the incident and modulated test signals, i.e., has a low dielectric loss factor over the desired frequency of operation. Further preferably, the tapered section 250 is sized to retain a single sample plug which may be on from 0.1 to 100 µl in volume, but is more preferably in the range from 1–10 µl. In one embodiment, the pipette tip 154 is fabricated from tetrafluoroethylene (Teflon®) having a maximum dielectric loss factor of approximately $1 \times 10^{-3}$ at 10 MHz. In the specific embodiment, the tapered section 250 measures 4.8 mm outer diameter 4.3 mm inner diameter at the top of the tapered section 250, tapering to 1.27 mm outer diameter and 0.8 mm inner diameter at the bottom of the tapered section 250, extending 50 mm therebetween. Similar materials such as polypropylene, polymers, hard plastics, glass, etc. can be used in alternative embodiments.

Preferably, the shape and diameter of the annular attachment flanges 210 and 240 permit engagement with standard pipette stems. In addition, the pipette tip 154 is designed to be disposable after a single or predetermined number of uses. More preferably, the sample handling surfaces of the pipette tip 154 in both illustrated embodiments of FIGS. 2A and 2B may be coated with compounds such as methylcellulose and polyethyleneglycol to prevent surface adhesion of molecular and/or cellular constituents occurring within the sample.

Bioassay Assembly Embodiments

Figure 3:
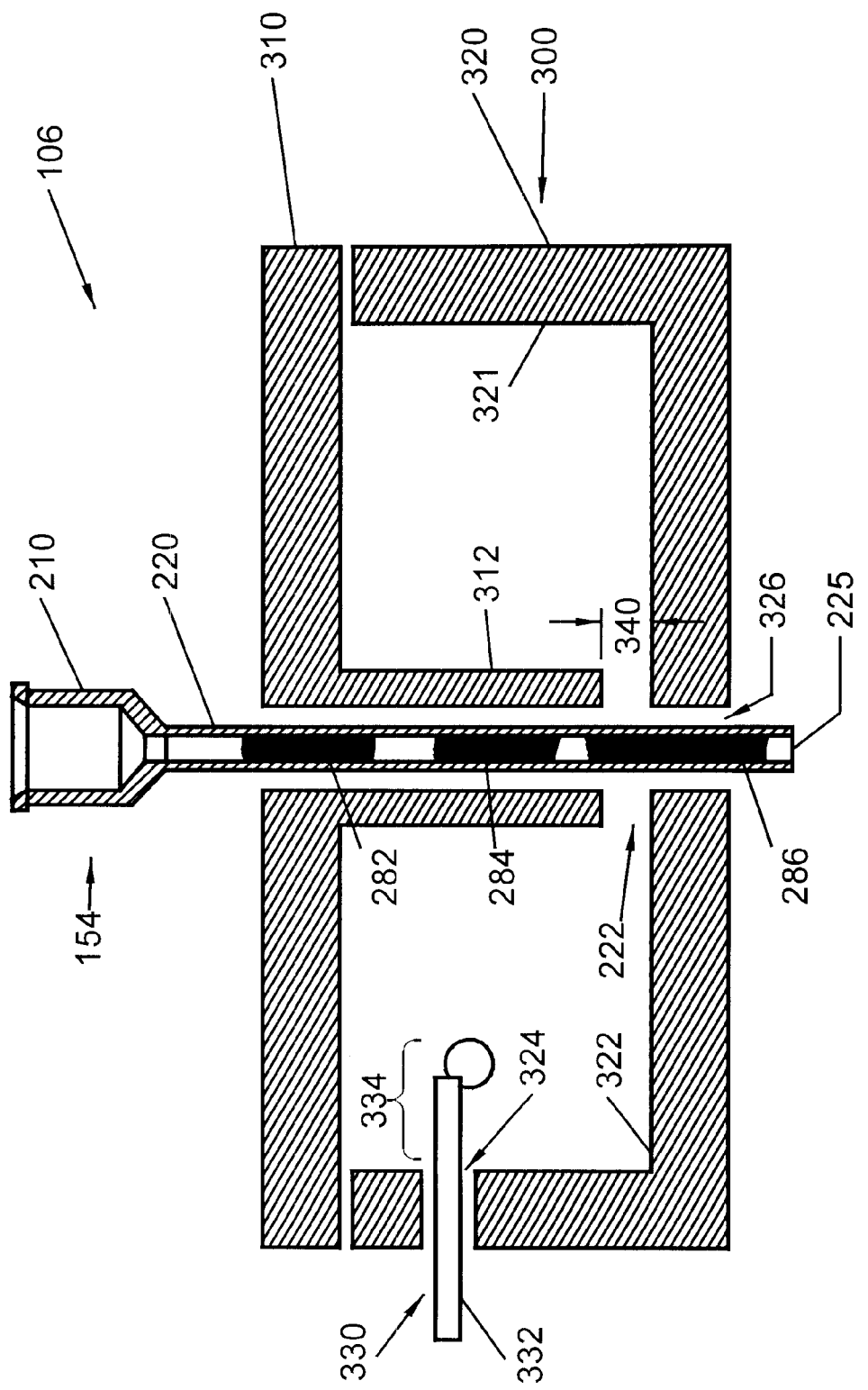
FIG. 3 illustrates a first embodiment of a pipette-loaded bioassay assembly in accordance with the present invention.

FIG. 3 illustrates a cross-sectional view of a pipette-loaded bioassay assembly 106 in accordance with one embodiment of the present invention (components used in previous drawings are labeled with their corresponding numerals). The embodiment of FIG. 3 employs a reentrant cavity configured to focus the intensity of the incident test signal into a detection region within the reentrant cavity, and a needle pipette tip operable to sequentially advance pre-aspirated sample plugs through the detection region. This configuration enables a highly accurate molecular and cellular event characterization process of multiple sample plugs since it obviates the need to move the pipette tip between successive measurements which could produce measurement error.

The bioassay assembly 106 includes a reentrant cavity assembly 300 and a needle pipette tip 154 as shown in FIG. 2A. The reentrant cavity assembly 300 includes a top member 310, and a cavity body 320. The top member 310 includes a hollow reentrant post 312 extending from the bottom interior surface. The cavity body 320 includes the cavity sidewall 321 and the cavity floor 322. The cavity sidewall 321 includes a measurement probe access port 324 and the cavity floor 322 includes a pipette tip exit port 326. The top member 310 is removably attached to the cavity body 320, using, e.g., screws threadingly engaged into the cavity body 320.

A probe assembly 330 having a transmission structure 332 and a measurement probe 334 enters into the reentrant cavity assembly 300 through the measurement probe access port 324. In one embodiment, the transmission structure 332 is a coaxial transmission line having an outer ground shield, a center conductor and a dielectric layer (typically tetrafluoroethylene (Teflon®) extending between the outer ground shield and the center conductor. In this embodiment, the measurement probe 334 consists of a coaxial cable portion having an extending center conductor portion which forms a loop and is shorted to the coaxial cable's ground shielding. In other embodiments, the measurement probe 334 may consist of an open-ended section of coaxial cable (or any other two-conductor TEM structure) or the aperture port of a waveguide transmission structure. These embodiments of the measurement probe 334, as well as other structures used to electromagnetically couple signals into connecting structures are described in the text *Foundations of Microwave Engineering*, R. E. Collin, (McGraw-Hill) 1966, incorporated herein by reference.

A detection region 340, through which a large number of electromagnetic field lines pass, is formed longitudinally between the reentrant post bottom and the cavity floor 322. The construction and operation of the reentrant cavity assembly 300 is further described in applicant's concurrently filed application entitled "Reentrant Cavity Bioassay for Detecting Molecular and Cellular Events," (Ser. No. 09/880,311), and is incorporated herein by reference.

The needle pipette tip 154 is vertically positioned so that the signal interrogation region 222 coincides with the detection region 340. In a specific embodiment, the needle pipette tip 154 is initially aspirated with three air-separated sample plugs 282, 284, and 286 through the use of the automated sample processor 104 (FIG. 1). Sample plugs 282, 284, and 286 may be of different compositions; for example, sample plug 282 may consist of a buffer solution, sample plug 284 may consist of a specific ligand in the aforementioned buffer solution 282, and sample plug 286 may consist of a protein suspected of having a binding affinity to the aforementioned ligand and the ligand itself. In this instance, the automated sample processor draws each sample plug from its respective reservoir, preferably introducing an air gap into the pipette tip 154 between subsequent sample plugs 282, 284, and 286 in order to prevent mixing between plugs. The automated sample processor may be preprogrammed to move the pipette tip 154 over respective sample reservoirs and obtain a predetermined volume (e.g., 1–10 µ) of sample therefrom.

Once aspirated with the desired number of sample plugs, the automated sample processor positions the pipette tip 154 over the reentrant post 312 and lowers the pipette tip 154 through the pipette tip exit port. In a specific embodiment, the last sample plug 286 is aspirated into the signal interrogation region 222 of the pipette tip 154, and the pipette tip 154 is lowered into the reentrant post 312 such that the last sample plug 286 is within the cavity's detection region 340.

Once the cavity's resonant frequency is measured with the sample plug 286 within the detection region 340, the automated sample processor supplies sufficient positive pressure to advance the second sample plug 284 to the detection region 340 (or negative pressure may be supplied to the bottom opening 225), thereby dispensing the previously measured sample plug 286 to waste. This process repeats until all of the plugs are measured and dispensed, at which point the automated sample processor discards the pipette tip 154. The automated sample processor may be programmed to load a new needle and repeat the foregoing steps as desired.

Figure 4:
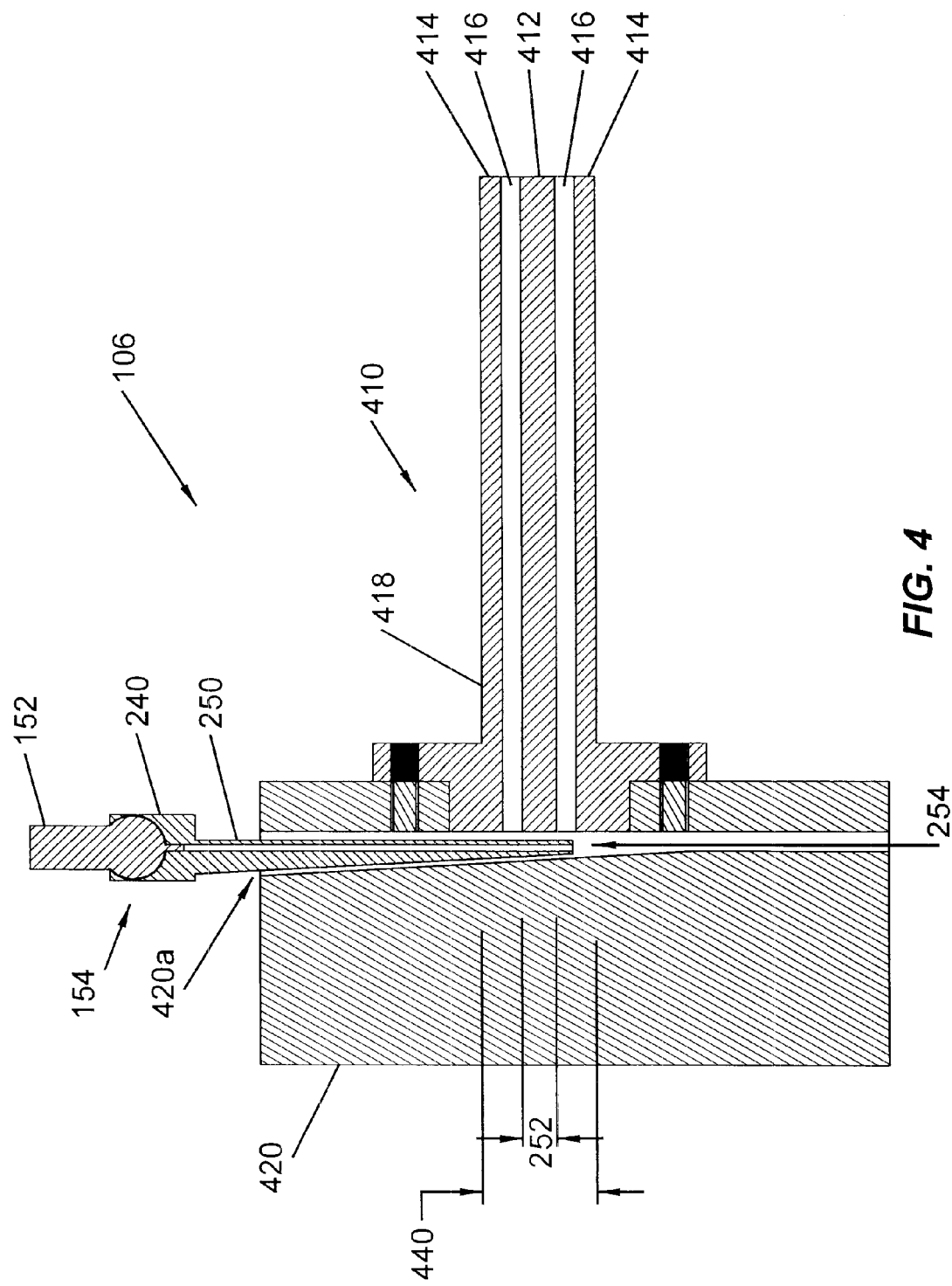
FIG. 4 illustrates a second embodiment of a pipette-loaded bioassay assembly in accordance with the present invention.

FIG. 4 illustrates a cross-sectional view of a second embodiment of the pipette-loaded bioassay assembly 106 in accordance with the present invention (components used in previous drawings are labeled with their corresponding numerals). This embodiment uses an open-ended coaxial measurement probe to interrogate sample solution contained within a tapered pipette tube. This configuration provides a simple, highly automated test platform employable in high-throughput systems.

The bioassay assembly 106 includes an open-ended coaxial measurement probe 410, a tapered pipette tip 154 as illustrated in FIG. 2B, and a temperature control plate 420. The open-ended coaxial measurement probe 410 includes center conductor 412, a ground plane in the form of outer shielding 414, a dielectric layer 416 extending between the center conductor 412 and the ground plane 414, and one or more hollowed-out dielectric discs 418 used to separate the center conductor 412 and the ground planes 414. At the openended cross section of the coaxial measurement probe, the annular region between the center conductor 412 and the outer shielding 414 defines the detection region 440 of the bioassay assembly 106 through which a majority of the test signal fields lines pass during measurement. In a specific embodiment, the center conductor 412 is copper and measures 2.8 mm in outside diameter, and the outer shielding is copper and measures 6.4 mm in inside diameter. The dielectric layer 416 consists substantially of air, the center conductor 412 being separated from the outer shielding 414 by tetrafluoroethylene (Teflon®) hollowed-out discs 418, through which the center conductor 412 extends. The open-ended coaxial measurement probe 410 may consist of a resonant or non-resonant structure. The design and operation of the open-ended coaxial measurement probe 410 is provided in greater detail in the applicant's co-pending application Ser. No. 09/687,456 entitled "System and Method for Detecting and Identifying Molecular Events in a Test Sample," filed Oct. 13, 2000. Those skilled in the art of high frequency circuit design we appreciate that the coaxial measurement probe 410 may be realized in alternative TEM structures, or as a waveguide structure as well.

The tapered pipette tip 154 includes a flange assembly 240 releasably attached to a pipette stem 152, the pipette stem 152 operable to aspirate sample solution into the tapered pipette tip 154 via the bottom opening 254. In the illustrated embodiment, the tapered pipette tip 154 is wedged-shaped and has a substantially flat surface 250 adjacent to the coaxial resonant probe 410, whereby the sample interrogation region 252 is located within the detection region 440 of the bioassay assembly 106. More preferably, the sample interrogation region 252 is centered about the longitudinal axis of the center conductor 412. The amount of sample aspirated (typically 1–10 $\mu$l) is sufficient to fill the tapered pipette tip 154 to at least to the top level of the signal interrogation region 252. An air gap is preferably provided at the bottom of the pipette tip 154 in order to prevent sample contamination of the open-ended measurement probe.

A temperature control plate 420 is used to heat/cool the contained sample and the open-ended coaxial measurement probe 410 to a predefined temperature. In a specific embodiment, the temperature control plate 420 has a wedge-shaped surface 420a complementary to the wedge-shaped surface of the tapered pipette tip 154, thereby facilitating location of the pipette tip 154 adjacent to the coaxial measurement probe 410. In a specific embodiment the temperature control plate 420 is constructed from aluminum, although other thermally conductive materials such as brass, copper, and the like may be used in alternative embodiments under the present invention.

Figure 5:
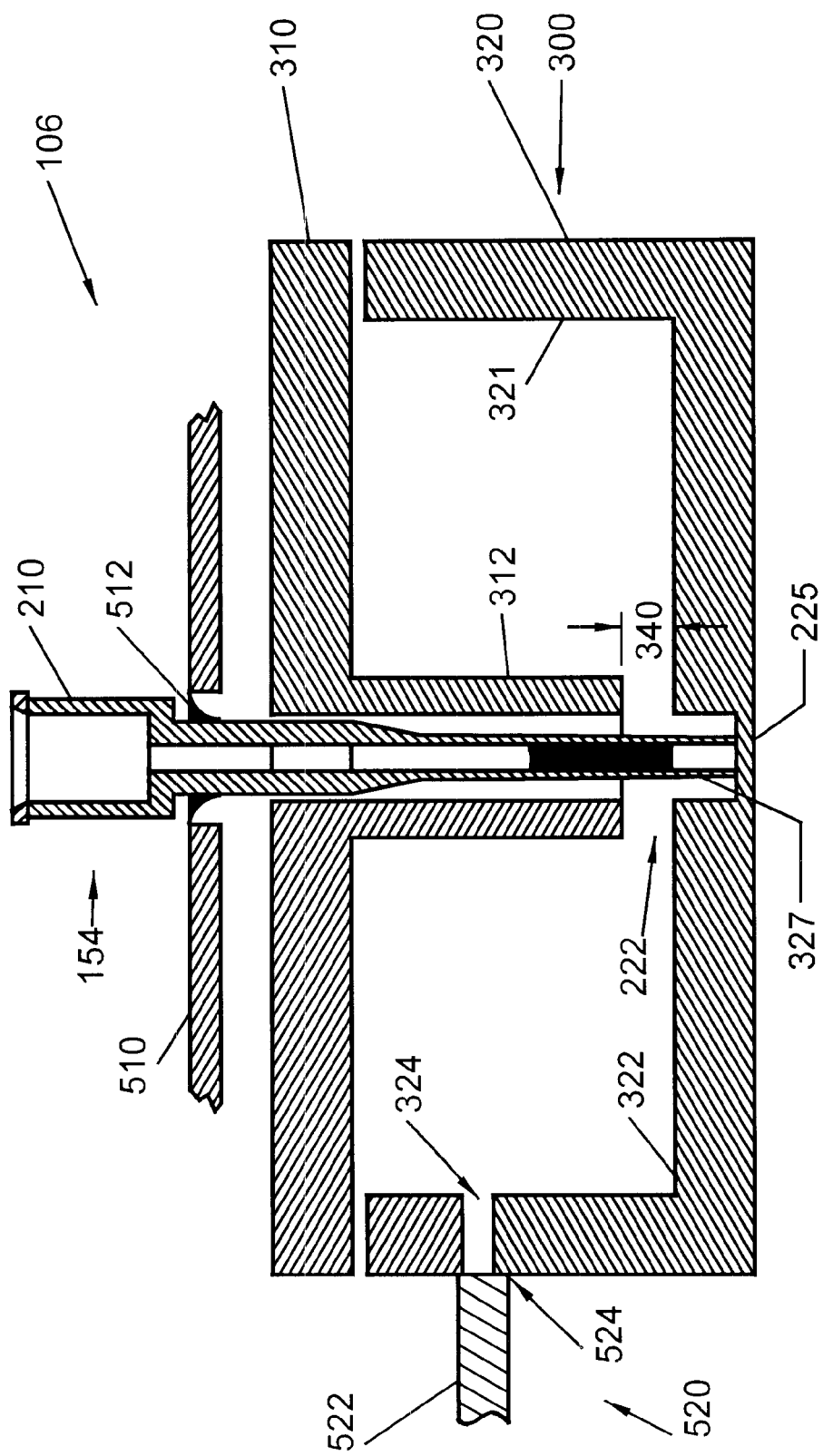
FIG. 5 illustrates a third embodiment of a pipette-loaded bioassay assembly in accordance with the present invention.

FIG. 5 illustrates a cross-sectional view of a third embodiment of the pipette-loaded bioassay assembly 106 in accordance with the present invention (components used in previous drawings are labeled with their corresponding numerals). This embodiment employs a thermally-enclosed reentrant cavity loaded with the needle pipette tip illustrated in FIG. 2A. This set up provides a temperature-controlled test platform useable in high-throughput systems.

The bioassay assembly 106 is located within a thermal enclosure 510 into which the needle pipette tip 154 extends via a silicon rubber septa membrane 512. The enclosure's internal temperature may be increased or decreased using conduction, convection, or radiating elements. A centering notch 327 disposed on the cavity floor 322 is used to laterally center the tapered pipette tip 154 within the reentrant post 312. A probe assembly 520 includes a waveguide transmission structure 522, the aperture port of which functions as the measurement probe 524. The waveguide aperture port 524 is operable to provide the incident test signal to, and preferably recover the modulated test signal from, the reentrant cavity 300. In an alternative embodiment, the reentrant cavity 300 may include a second measurement probe (waveguide or TEM type) to provide two-port measurement capability. The remaining illustrated features operate as described above.

During an exemplary operation, the automated sample processor 104 (FIG. 1) loads the pipette tip 154 onto the pipette stem 152 and the pipette assembly is positioned over a sample reservoir. The automated sample processor lowers the pipette tip into the sample reservoir and aspirates a predefined volume of sample (1–10 $\mu$l in one embodiment) through the bottom opening 225. In a preferred embodiment, an air gap is subsequently aspirated into the pipette tip 154 to prevent sample contamination of the centering notch 327.

Once the pipette tip 154 is loaded onto the pipette stem and aspirated with sample, the pipette tip 154 is positioned into the reentrant cavity as shown. The aspirated sample is sufficient to extend into the sample interrogation region 222 of the pipette tip 154, and the position of the sample interrogation region 222 coincides with the location of the detection region 340 of the reentrant cavity 300. The automated network analyzer 108 (FIG. 1) generates and launches an incident test signal which the transmission structure 520 guides to the measurement probe 522. The measurement probe 522 supplies the incident test signal to the reentrant cavity 300, and the reentrant post 312 functions to focus the field lines to the detection region 340. The molecular or cellular events occurring within the detection region 340 modulate these field lines, producing in response a modulated test signal. The measurement probe 522 (or a second measurement probe if a two-port measurement is made) recovers the modulated test signal, and the transmission structure 520 guides it to the automated network analyzer 108 where it is processed and compared to other modulated test signals as described above. Upon completion of the signal interrogation, the automated sample processor 104 lifts the pipette tip 154 from the reentrant cavity 300, positions the pipette tip 154 over a predefined waste area on the sample deck and ejects the pipette tip 154 therein. Alternatively, the automated sample processor 104 operates to dispense the sample plug into its source reservoir, thereby recovering the sample for possible use in a secondary assay for instance. In a specific embodiment, the automated sample processor 104 and network analyzer 108 are controlled by the computer 102 to perform the foregoing processes on a "sample deck" (not shown), the sample deck incorporating one or more sample reservoirs and reentrant cavities. The computer 102 may be preprogrammed to repeat the described processes as needed.

The test system 100 may further include sample sensor (not shown) operable to detect the presence of a sample plug within the detection region. An exemplary sensor may consist of an optical or infrared source positioned to illuminate a sample plug within the detection region, and a detector located to receive the light signal through the pipette tip 154. The detector senses the presence of a sample plug within the detection region when the sample plug interrupts the beam, causing a change in light intensity received at the detector. Alternatively, the automated network analyzer 108 can be used as the sample sensor. In this embodiment, the signal response of the bioassay assembly is characterized when an exemplary air plug is located within detection region, and the response stored. Subsequently, the automated network analyzer 108 monitors and compares the measured signal response to the stored air plug response in real time. When the measured and signal responses correlate, an air gap exists within the detection region. Subsequently, the automated sample processor 104 applies negative or positive pressure thereby positioning the adjacent sample plug within the detection region of the bioassay assembly. The instructions and data necessary to execute these functions may be preprogrammed into the computer 102.

While the above is a complete description of possible embodiments of the invention, various alternatives, modifications, and equivalents can be used. For instance, the present invention may be practiced by using the described pipette tip 154 in combination with bioassay devices previously described in the applicant's co-pending patent applications, such as application Ser. No. 09/365,978 entitled "Test Systems and Sensors for Detecting Molecular Binding Events," filed Aug. 2, 1999; application Ser. No. 09/687,456 entitled "System and Method for Detecting and Identifying Molecular Events in a Test Sample," filed Oct. 13, 2000; Ser. No. 09/775,718 entitled "Bioassay Device for Detecting Molecular Events," filed Feb. 1, 2001, and the applicant's commonly-owned application entitled "Reentrant Cavity Bioassay for Detecting Molecular and Cellular Events," concurrently filed herewith. Further, all publications and patent documents recited in this application are incorporated by reference in their entirety for all purposes to the same extent as if each individual publication and patent document was so individually denoted.

Applicant's commonly owned, concurrently filed application entitled "Reentrant Cavity Bioassay for Detecting Molecular or Cellular Events," (Ser. No. 09/880,311) is herein incorporated by reference for all purposes.

The following commonly owned, co-pending applications are herein incorporated by reference in their entirety for all purposes:

Ser. No. 09/243,194 entitled "Method and Apparatus for Detecting Molecular Binding Events, filed Feb. 1, 1999;

Ser. No. 09/365,578 entitled "Method and Apparatus for Detecting Molecular Binding Events," filed Aug. 2, 1999;

Ser. No. 09/365,978 entitled "Test Systems and Sensors for Detecting Molecular Binding Events," filed Aug. 2, 1999;

Ser. No. 09/365,581 entitled "Methods of Nucleic Acid Analysis," filed Aug. 2, 1999;

Ser. No. 09/365,580 entitled "Methods for Analyzing Protein Binding Events," filed Aug. 2, 1999;

Ser. No. 09/687,456 entitled "System and method for detecting and identifying molecular events in a test sample," filed Oct. 13, 2000;

Ser. No. 60/248,298 entitled "System and method for real-time detection of molecular interactions," filed Nov. 13, 2000;

Ser. No. 09/775,718 entitled "Bioassay device for detecting molecular events," filed Feb. 1, 2001;

Ser. No. 09/775,710 entitled "System and method for detecting and identifying molecular events in a test sample using a resonant test structure," filed Feb. 1, 2001;

Ser. No. 60/268,401 entitled "A system and method for characterizing the permittivity of molecular events," filed Feb. 12, 2001;

Ser. No. 60/275,022 entitled "Method for detecting molecular binding events using permittivity," filed Mar. 12, 2001;

Ser. No. 60/277,810 entitled "Bioassay device for Detecting Molecular Events," filed Mar. 21, 2001; and Ser. No 09/837,898 entitled "Method and Apparatus for Detection of Molecular Events Using Temperature Control of Detection Environment," filed Apr. 18, 2001.

What is claimed is:

1. A method for detecting a molecular or cellular event in a sample solution using a pipette-loaded bioassay assembly, the method comprising the steps of:

providing a measurement probe operable to support the propagation of an electromagnetic signal at a frequency at or above 1 MHz and below 1000 GHz, the measurement probe comprising a probe head located at a proximate end of the measurement probe and a connecting end located at a distal end of the measurement probe, the connecting end configured to receive an incident test signal from a signal source and the probe head configured to launch the incident test signal;

aspirating a pipette tip with a sample plug comprising a predefined volume of the sample solution, the pipette tip comprising a sample interrogation region formed from a material that is substantially transparent to the incident test signal, wherein at least a portion of the aspirated sample plug is contained within the sample interrogation region of the pipette tip;

positioning the pipette tip such that the sample interrogation region is electromagnetically coupled to the measurement probe;

illuminating the sample interrogation region of the pipette tip with the incident test signal, whereby the incident test signal is launched from the probe head and electromagnetically couples through the sample interrogation region of the pipette tip to the molecular or cellular event occurring within the sample plug, wherein the interaction of the incident test signal with the molecular or cellular event produces a modulated test signal; and analyzing said modulated test signal to detect said molecular or cellular event.

2. The method of claim 1, wherein said analyzing step comprises:

recovering the modulated test signal;

ascertaining a measured signal response;

comparing the measured signal response to a stored signal response, the stored signal response corresponding to a known molecular or cellular event;

identifying the molecular or cellular event occurring within the sample plug as the molecular or cellular event occurs within the sample plug.

3. The method of claim 1, wherein said analyzing modulated test signal step comprises ascertaining impedance parameters of the bioassay assembly.

4. The method of claim 1, wherein said analyzing said modulated test signal step comprises ascertaining impedance parameters of the bioassay assembly.

5. The method of claim 1, wherein said analyzing said modulated test signal step comprises:

converting the modulated test signal to a first permittivity value; and obtaining a delta permittivity difference value comprising the difference between the first permittivity value and a second, previously obtained permittivity value.

6. The method of claim 1, further comprising the step of providing a reentrant cavity comprising a reentrant post extending from a fist interior surface and terminating proximate to a second interior surface, the gap between the termination of the reentrant post and the second surface defining a detection region.

7. The method of claim 1, wherein said providing a measurement probe step comprises providing a coaxial line having a center conductor, a ground shield, and a dielectric layer interposed between the c enter conductor and the ground shield, wherein the probe head comprises an open-ended cross section of the coaxial line.

8. The method of claim 6, wherein positioning the pipette tip comprises positioning the sample interrogation region of the pipette tip within the detection region of the reentrant cavity.

9. The method of claim 7, wherein positioning the measurement probe comprises centering the signal interrogation region of the pipette tip along the longitudinal axis of the coaxial line.

10. The method of claim 1, wherein aid electromagnetic signal has a frequency in a range from 1 MHz to 1000 GHz.

11. The method of claim 10, wherein said electromagnetic signal has a frequency in a range from 10 MHz to 1000 GHz.

12. The method of claim 11, wherein said electromagnetic signal has a frequency in a range from 10 MHz to 110 GHz.

* * * * *